US009451902B2

(12) United States Patent
Stocker (10) Patent No.: US 9,451,902 B2
(45) Date of Patent: Sep. 27, 2016

(54) MEDICAL IMAGING APPARATUS (71) Applicant: Stefan Stocker, Großenseebach (DE)

(72) Inventor: Stefan Stocker, Großenseebach (DE)

(73) Assignee: Siemens Aktiengesellschaft, Munich (DE)

(*) Notice: Subject to any disclaimer, the term of this patent is extended or adjusted under 35 U.S.C. 154(b) by 1036 days.

(21) Appl. No.: 13/628,822

(22) Filed: Sep. 27, 2012

(65) Prior Publication Data

US 2013/0082712 A1    Apr. 4, 2013

(30) Foreign Application Priority Data

Sep. 30, 2011 (DE) .......... 10 2011 083 837

(51) Int. Cl.
*G01R 33/341* (2006.01)
*A61B 5/055* (2006.01)
*G01R 33/48* (2006.01)
*G01T 1/29* (2006.01)
*G01T 1/16* (2006.01)
(Continued)

(52) U.S. Cl.
CPC ............ *A61B 5/055* (2013.01); *A61B 5/0035* (2013.01); *A61B 6/037* (2013.01); *A61B 6/4258* (2013.01); *A61B 6/4417* (2013.01); *G01R 33/481* (2013.01); *G01T 1/1603* (2013.01); *G01T 1/2985* (2013.01); *A61B 6/4266* (2013.01); *A61B 6/5247* (2013.01); *G01R 33/4812* (2013.01)

(58) Field of Classification Search
CPC ............ G01R 33/481; G01R 33/3806; G01R 33/4812; A61B 6/037; A61B 6/4417; A61B 5/0035; A61B 5/055; A61B 6/4258; A61B 6/5247; G01T 1/1603; G01T 1/362; G01T 1/2985

USPC .................. 324/318, 322; 600/411
See application file for complete search history.

(56) References Cited

U.S. PATENT DOCUMENTS 6,556,012 B2 *  4/2003  Yamashita ......... G01R 33/3854
                                                            324/307
2004/0061499 A1   4/2004  Stocker
(Continued)

FOREIGN PATENT DOCUMENTS

CN    101254100 A    9/2008
DE    10245942 A1    4/2004
(Continued)

OTHER PUBLICATIONS

Katsunuma, A., et al. "Quiet MRI with novel acoustic noise reduction." Magnetic Resonance Materials in Physics, Biology and Medicine 13.3 (2001): 139-144.*
(Continued)

*Primary Examiner* — Melissa Koval
*Assistant Examiner* — Rishi Patel
(74) *Attorney, Agent, or Firm* — Harness, Dickey & Pierce (57) ABSTRACT A medical imaging apparatus includes a first imaging modality which is formed by a magnetic resonance apparatus and which comprises a cylindrical gradient coil unit, and a further imaging modality which comprises a detector unit. The detector unit of the further imaging modality is supported in a radial direction within an area surrounded by the gradient coil unit and an annular gap is disposed between the detector unit of the further imaging modality and the gradient coil unit. The further imaging modality includes a pressure unit which is disposed in the annular gap between the detector unit of the further imaging modality and the gradient coil unit.

14 Claims, 3 Drawing Sheets (51) Int. Cl.
  *A61B 6/03* (2006.01)
  *A61B 6/00* (2006.01)
  *A61B 5/00* (2006.01)

(56) References Cited

U.S. PATENT DOCUMENTS

| | | | |
|---|---|---|---|
| 2007/0182415 A1* | 8/2007 | Schuster | G01R 33/28 324/318 |
| 2008/0208032 A1 | 8/2008 | Schuster et al. | |
| 2008/0208035 A1 | 8/2008 | Nistler et al. | |
| 2009/0221903 A1 | 9/2009 | Corbeil et al. | |
| 2012/0313643 A1* | 12/2012 | Edelstein | G01R 33/3854 324/318 |

FOREIGN PATENT DOCUMENTS

| | | |
|---|---|---|
| DE | 102007009180 A1 | 8/2008 |
| DE | 102007009184 A1 | 8/2008 |
| DE | 102008012312 A1 | 1/2010 |
| EP | 1085336 A2 | 3/2001 |

OTHER PUBLICATIONS

German Office Action for German Application No. DE 102011083837.6 dated Jun. 11, 2012.
Priority Document German Application No. DE 102011083837.6 filed Sep. 30, 2011.
Chinese Office Action and English translation thereof dated Aug. 7, 2015.

* cited by examiner

FIG 4

MEDICAL IMAGING APPARATUS

PRIORITY STATEMENT

The present application hereby claims priority under 35 U.S.C. §119 to German patent application number DE 10 2011 083 837.6 filed Sep. 30, 2011, the entire contents of which are hereby incorporated herein by reference.

FIELD

At least one embodiment of the present invention generally relates to a medical imaging apparatus with a first imaging modality which is formed by a magnetic resonance apparatus and which comprises a cylindrical gradient coil unit, and a further imaging modality which comprises a detector unit, wherein the detector unit of the further imaging modality is supported in a radial direction within an area surrounded by the gradient coil unit and an annular gap is disposed between the detector unit of the further imaging modality and the gradient coil unit.

BACKGROUND

In medical imaging apparatuses having two imaging modalities a difficulty arises of combining the two imaging modalities, especially detector units of the two imaging modalities in a suitable manner, so as to preferably prevent the two detector units impeding each other during operation of the medical imaging apparatus for medical imaging examinations. If a first imaging modality is formed by a magnetic resonance apparatus and a second imaging modality by a PET apparatus, a PET detector of the PET apparatus is integrated to save space within a magnet unit of the magnetic resonance apparatus. The PET detector unit is disposed here on a support unit of the PET apparatus which is disposed in a radial direction between a high-frequency coil unit and a gradient coil unit of the magnetic resonance apparatus. In addition an annular gap is disposed between the PET detector unit and the gradient coil unit.

However with such an arrangement of the PET detector unit with the gradient coil unit the result can be an undesired vibration coupling between the gradient coil unit and the PET detector unit, such as for example by way of the transmission of airborne sound waves and/or a transmission of body-borne sound waves. This can lead to undesired noise stress for the patient. Furthermore, as a result of the vibrations the service life and/or a function of the PET detector unit can also be adversely affected, such as for example a service life and/or a function of electronics of the PET detector unit and/or copper screening of the PET detector unit.

SUMMARY

At least one embodiment of the present invention provides a medical imaging apparatus which comprises a magnetic resonance apparatus and a further imaging modality, in which a detector unit of the further imaging modality is effectively protected against transmission of vibrations. Advantageous embodiments are described in the subclaims.

At least one embodiment of the invention is directed to on a medical imaging apparatus with a first imaging modality which is formed by a magnetic resonance apparatus and which comprises a cylindrical gradient coil unit, and a further imaging modality which comprises a detector unit, whereby the detector unit of the further imaging modality is supported in a radial direction within an area surrounded by the gradient coil unit and an annular gap is disposed between the detector unit of the further imaging modality and the gradient coil unit.

BRIEF DESCRIPTION OF THE DRAWINGS

Further advantages, features and details of the invention emerge from the exemplary embodiments described below as well as with reference to the drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention is directed to on a medical imaging apparatus with a first imaging modality which is formed by a magnetic resonance apparatus and which comprises a cylindrical gradient coil unit, and a further imaging modality which comprises a detector unit, whereby the detector unit of the further imaging modality is supported in a radial direction within an area surrounded by the gradient coil unit and an annular gap is disposed between the detector unit of the further imaging modality and the gradient coil unit.

It is proposed that the further imaging modality has a pressure unit which is disposed in the annular gap between the detector unit of the further imaging modality and the gradient coil unit. Preferably a pressure can be can be generated by way of the pressure unit in the annular gap which acts in particular on the detector unit of the further imaging modality. One effect of this pressure is to exert an even pressure force on individual detector elements and/or crystals of the detector unit and thereby have a stiffening effect on a structure of the detector unit of the further imaging modality, wherein the detector unit of the further imaging modality is preferably supported on a carrier unit of the further imaging modality. In this way a damping of vibrations and/or sound waves can be undertaken, with vibration amplitudes, especially wideband vibration amplitudes of up to 30 dB, able to be damped in such cases.

Furthermore a reduction of a noise coupling and in association with this a reduction of a noise emission in operation of the medical imaging device can be achieved. In addition, as a result of a reduction of the transmission of vibrations, a risk of a defect of the detector unit of the further imaging modality can be reduced and in this way the service life of the detector unit significantly increased. In this context a further imaging modality is especially to be understood as a positron emission apparatus (called a PET apparatus hereafter), wherein the PET apparatus comprises a PET detector unit. The PET detector unit preferably covers the Field of View (FoV) generated by the magnetic resonance apparatus. As an alternative to this the further imaging modality can also be formed by a CT apparatus and/or further medical imaging apparatuses. An area extending in the radial direction surrounded by the gradient coil unit is especially to be understood as an area which is surrounded by the cylinder jacket of the gradient coil unit.

Furthermore it is proposed that the pressure unit has a single pressure chamber which in an installed position completely covers the detector unit of the further imaging modality. This enables an especially even pressure to be generated so that the same uniform pressure acts on all detector elements of the detector unit, such as on individual PET detector elements for example. In this way tension forces which could act with a number of pressure chambers of the pressure unit on the detector unit and/or a carrier unit of the further imaging modality for supporting the detector unit, for example with different pressures within the different pressure chambers, are advantageously avoided. In addition the entire detector unit of the further imaging modality can advantageously be protected from direct coupling with the gradient coil unit. Preferably the single pressure chamber is embodied in a cylindrical shape.

An especially advantageous damping of vibration amplitudes and/or reduction of the transmission of sound waves can be achieved if the pressure unit has a pressure chamber with a pressure within the pressure chamber of at least 0.1 bar. By way of the pressure within the pressure chamber of at least 0.1 bar a pressure force can act on detector elements of the detector unit which corresponds to approximately 4.7 times a weight force of the individual detector elements of the detector unit. The pressure force acting on the individual detector elements increases in this case proportionally to the pressure within the pressure chamber. Especially preferably the pressure within the pressure chamber however has a minimum value of 0.3 bar.

An advantageous protection of individual components of the detector unit, such as electronics and/or individual detector elements of the detector unit for example, against damage as a result of excessive pressure force can be achieved if the pressure unit has a pressure chamber with a pressure within the pressure chamber of a maximum of 1.0 bar. Preferably however the pressure within the pressure chamber has a maximum value of 0.7 bar and especially preferably a maximum value of 0.5 bar.

If the pressure unit has a pressure chamber which has an envelope with a variable shape, an especially low-cost and also flexible pressure chamber can be provided for the medical imaging apparatus. In addition the pressure chamber in this case can also be embodied to be particularly adaptable, especially to a geometrical dimension of the space within the annular gap available for the pressure chamber, so that an exact adaptation of the pressure chamber to the available space can be achieved and/or the available space can be filled in a constructively simple manner by the pressure chamber. The envelope of pressure chamber is preferably formed from a foil such as for example a foil made of a polyurethane material, wherein the foil is welded together into a desired shape, especially into a cylindrical pressure chamber.

It is further proposed that the pressure chamber is able to be filled with a fluid, which advantageously enables the pressure chamber to be especially adapted to a dimension of the annular gap. The fluid can be formed from all fluids appearing sensible to the person skilled in the art such as liquids and/or gases for example. Especially advantageously however the fluid is formed by air, so that the pressure unit can be implemented at especially low cost. In addition high availability of the fluid can be achieved if the latter is formed by air.

In a further embodiment of the invention it is proposed that the pressure unit has a pressure regulation unit, through which advantageously a pressure can be set within the pressure chamber. Preferably the pressure regulation unit comprises a pressure supply unit such as a compressed air pump for example.

Furthermore it is proposed that the pressure unit features at least one sensor element for monitoring a characteristic pressure value through which an advantageous pressure regulation for the pressure chamber as a function of a current pressure within the pressure chamber can be achieved. Preferably the at least one sensor element is embodied and/or disposed within the pressure unit such that the sensor element detects the characteristic pressure value of a pressure within the pressure chamber.

It is further proposed that the pressure unit features an alarm signal unit which generates an alarm signal when the pressure falls below a lower limit value and/or exceeds an upper limit value and outputs this alarm signal. In this case an operator can be alerted especially quickly to an incorrect pressure within the pressure unit, especially within a pressure chamber of the pressure unit. The alarm signal unit can comprise an optical alarm output means and/or an acoustic alarm output means for this purpose for output of an optical alarm signal and/or of an acoustic alarm signal.

In an advantageous development of an embodiment of the invention it is proposed that the further imaging modality has a carrier unit, for supporting the detector unit of the further imaging modality and an attachment unit for attaching the pressure unit to the carrier unit of the further imaging modality. The pressure unit, especially a pressure chamber of the pressure unit, can be disposed in a precise position in relation to the detector unit supported on the carrier unit of the further imaging modality within the annular gap of the medical imaging apparatus. In addition the pressure unit slipping out of place during introduction and/or installation of the carrier unit together with the detector unit of the further imaging modality can be advantageously prevented. Especially advantageously in this case the attachment unit comprises a latching unit and/or a further attachment unit for a releasable and/or detachable attachment of the pressure unit to the carrier unit. As an alternative or in addition the attachment unit can also comprise an adhesion unit etc. preferably the pressure chamber of the pressure unit is attached in an empty state to the carrier unit of the further imaging modality and is only filled with a fluid, especially with compressed air, in an installed position within the annular gap.

It is further proposed that an attachment of the pressure unit by way of the attachment unit to the carrier unit of the further imaging modality is undertaken before installation of the carrier unit of the further imaging modality within the annular gap. The pressure unit can be disposed in a mechanically simple manner on the carrier unit of the further imaging modality, especially on the detector unit. In addition in this case the pressure unit, to screen the detector unit of the further imaging modality against a transmission and/or a coupling of vibrations can be positioned particularly precisely. Especially advantageously the pressure unit can subsequently be installed in the annular gap in a position installed on the carrier unit of the further imaging modality, so that the installation of the pressure unit and the carrier unit together with the detector unit can be undertaken in an especially time-saving manner in a joint working step. The pressure chamber is preferably filled with the fluid only after installation of the pressure chamber within the annular gap.

Furthermore it is proposed that the attachment unit has at least one attachment element for bracing a pressure chamber of the pressure unit on the detector unit of the further imaging modality. In this case the pressure unit, especially a pressure chamber of the pressure unit having an envelope with a variable shape, can especially be disposed without any folds on the detector unit and the carrier unit and in this way risk of damage to the detector unit and/or the pressure chamber can be advantageously minimized. In addition undesired slipping out of place of the tension and pressure chamber during introduction of the pressure chamber can be advantageously prevented.

Especially advantageously the attachment unit has at least one attachment element for releasably attaching a pressure chamber of the pressure unit to the carrier unit of the further imaging modality. In this case the one pressure chamber, for example for maintenance work and/or repair work on the detector unit of the further imaging modality, can be removed and/or released in an especially simple manner from the carrier unit and the detector unit of the further imaging modality. In this context a releasable attachment of the pressure chamber is especially to be understood as an attachment of the pressure chamber of the pressure unit to the carrier unit of the further imaging modality in which the pressure chamber is able to be removed or dismantled from the carrier unit, wherein through a release of the attachment or through a dismantling of the pressure chamber of the pressure unit from the carrier unit of the further imaging modality, neither the pressure unit, especially the pressure chamber of the pressure unit, nor the detector unit of the further imaging modality and/or the carrier unit of the further imaging modality for supporting the detector unit adversely affects its operability.

In an advantageous development of an embodiment of the invention it is proposed that the attachment unit has at least two attachment elements which make a connection to attach the pressure unit to the carrier unit of the further imaging modality, wherein a first of the at least two attachment elements is disposed on the pressure unit and a second of the at least two attachment elements is disposed on the carrier unit of the further imaging modality. Preferably the pressure unit, especially a pressure chamber of the pressure unit, is attached to the carrier unit of the further imaging modality by way of a latching connection, especially a releasable latching connection, between the two attachment elements, so that the pressure unit can be taken off and/or removed especially simply from the carrier unit for maintenance work on the detector unit of the further imaging modality for example. The two attachment elements can for example be formed by fabric strips with latching elements disposed thereon, wherein the latching elements for example can at least partly comprise a Velcro connection.

Figure 1:
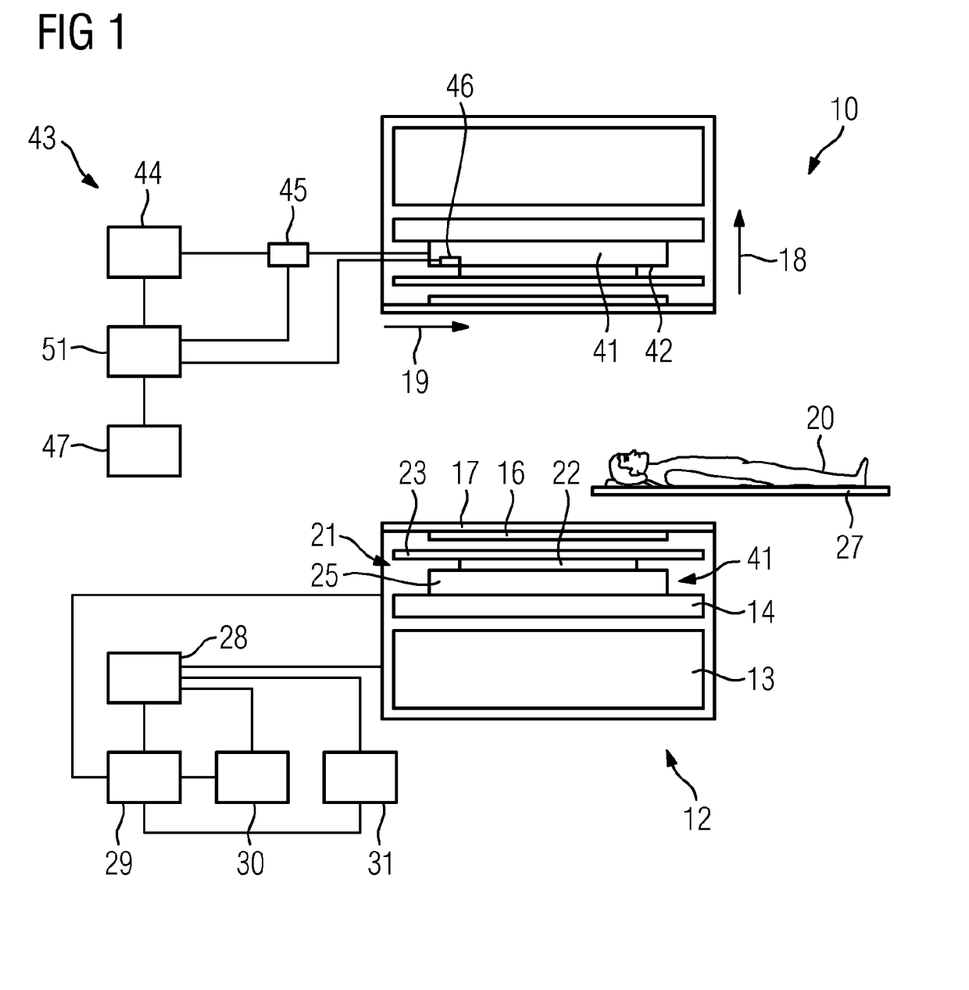
FIG. 1 shows an inventive imaging apparatus, comprising a magnetic resonance apparatus and a PET apparatus, in a schematic diagram.

FIG. 1 shows an inventive medical imaging apparatus 10 comprising a first imaging modality and a second imaging modality. The first imaging modality is formed by a magnetic resonance apparatus 11, which comprises a detector unit formed by a magnet unit 12 with a main magnet 13 for generating a strong and especially constant main magnetic field 19. The magnet unit 12 also features a cylindrical gradient coil unit 14 for generating magnetic field gradients which is used for a local encoding during imaging. Furthermore the magnet unit 12 comprises a high-frequency antenna unit 16 for exciting a polarization which occurs in the main magnetic field 19 generated by the main magnet 13. The high-frequency antenna unit 16 is supported on a cylindrical carrier unit 17 of the magnet unit 12, wherein the cylindrical carrier unit 17 is disposed in a radial direction 18 within the gradient coil unit 14.

The further imaging modality is formed by a PET apparatus 21 which has a detector unit formed by a PET detector unit 22 which is supported on a cylindrical carrier unit 23 of the PET apparatus 21. The carrier unit 23 of the PET apparatus 21 is disposed together with the PET detector unit 22 within the magnet unit 12 of the magnetic resonance apparatus 11, wherein the carrier unit 23 of the PET apparatus 21 is disposed together with the PET detector unit 22 in the radial direction 18 between the high-frequency coil unit 16 and the gradient coil unit 14 of the magnetic resonance apparatus 11. The PET detector unit 22 comprises a number of detector elements 24 (FIG. 2), which each comprise a photodiode array with an upstream array of lutetium oxyorthosilicate (LSO) crystals and an electrical amplifier unit. The PET detector unit 22 is disposed within the medical imaging apparatus 10 at a distance from the gradient coil unit 14, so that a cylindrical annular gap 25 is present in the radial direction 18 between the PET detector unit 22 and the gradient coil unit 14. The PET detector unit 22 also features copper screening not shown in any greater detail which is disposed on a surface of the PET detector elements facing towards the gradient coil unit 14. In addition screening units can be disposed between the individual detector components of the magnet unit 12 and the PET detector unit 22 for protection of the individual detector components.

The particular properties of the positron emitters and an annihilation of positrons are used for a PET examination in order to quantitatively determine a function of organs or of cell areas. In this case corresponding radio pharmaceuticals which are marked with radio nuclides are administered to a patient 20 before the PET examination. These radio nuclides emit positrons as they decay, which after a short distance interact with an electron, whereby a so-called annihilation of an electron-positron pair occurs. Because of an energy retention and a pulse retention two gamma quanta are created in the annihilation, which are sent out at the location of the annihilation in opposite directions which are offset by 180°. The two gamma quanta are detected by two opposing detector elements 24 within a specific time window (coincidence measurement), through which the location of the annihilation can be determined at a position on the connecting line between these two detector elements 24.

The medical imaging apparatus 10 in FIG. 1 also has a cylindrical area 26 to accommodate the patient 20, wherein the area 16 is surrounded in a circumferential direction by the cylindrical carrier unit 17 for supporting the high-frequency coil unit 16 of the magnet unit 12. The patient 20 can be pushed by way the patient couch 27 of the medical imaging apparatus 10 into the area 26. The patient couch 27 is disposed for this purpose so that it can be moved within the medical imaging apparatus 10.

For control of the two imaging modalities the medical imaging device 10 has a control unit 28. For this purpose the control unit 28 is connected via a data link not shown in any greater detail to the magnetic resonance apparatus 11 and the PET apparatus 21. The medical imaging apparatus 10 also has an evaluation unit 29 which evaluates both image data of the magnetic resonance apparatus 11 and also image data of the PET apparatus 21. Furthermore the medical imaging apparatus 10 includes an input unit 30 by means of which information and/or parameters can be input during a measurement process by an operator and a display unit 31 on which control information such as imaging parameters and results for example and/or presentation of medical imaging examinations can be displayed.

Figure 2:
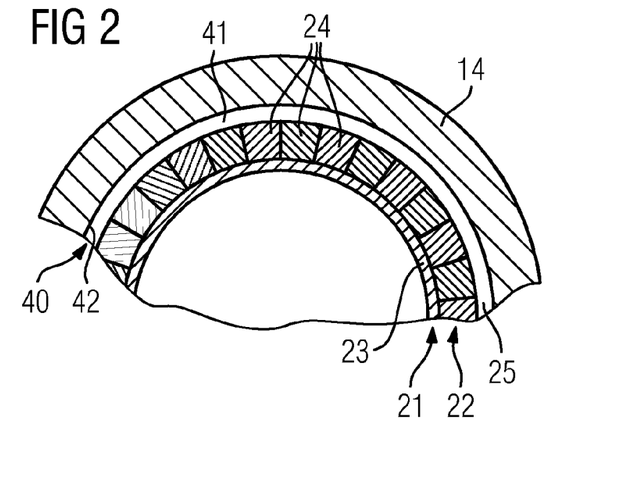
FIG. 2 shows a section through a part area of the medical imaging apparatus, with a pressure unit between a PET detector unit and a gradient coil unit of a magnetic resonance apparatus.

In addition the medical imaging apparatus 10 features a pressure unit 40 which is disposed in the annular gap 25 between the PET detector unit 22 and the gradient coil unit 14. The pressure unit 40 is enclosed by the PET apparatus 21 and has a single pressure chamber 41, which comprises an envelope 42 with a variable shape. The envelope 42 of the pressure chamber 41 is formed from a foil in this case, wherein the foil is formed from a polyurethane material which is welded at the edges to the pressure chamber 41. The pressure chamber 41 of the pressure unit 40 is disposed between the PET detector unit 22 and the gradient coil unit 14 such that the pressure chamber 41 completely covers the PET detector unit 22, especially a surface of the PET detector unit 22 facing towards the gradient coil unit 14. The pressure chamber 41 is disposed between this surface of the PET detector unit 22 and the gradient coil unit 14 along the entire surface of the PET detector unit 22 facing towards the gradient coil unit 14 such that a uniform pressure is exerted by the pressure chamber 41 on all detector elements of the PET detector unit 22.

Furthermore the pressure unit 40 has a pressure regulation unit 43, comprising a pressure supply unit 44, a valve unit 45 and at least one sensor element 46. The pressure supply unit 44 includes an air pressure pump by way of which a fluid formed by air is introduced into the pressure chamber 41 of the pressure unit 40. A pressure of the fluid within the pressure chamber 41 has a value at least between 0.1 bar and a maximum of 1.0 bar. Especially preferably however the pressure of the fluid within the pressure chamber 41 has a value between 0.3 bar and 0.45 bar. By way of the valve unit 45 undesired excess pressure can be vented from the pressure chamber 41, wherein the valve unit 45 is controlled by a control unit 51 of the pressure regulation unit 43. The pressure supply unit is likewise controlled by the control unit 51 of the pressure regulation unit 43.

By way of the sensor element 46 of the pressure regulation unit 43 at least one characteristic pressure value of a pressure within the pressure chamber 41 is detected. The sensor element 46 can be disposed for this purpose at least partly within the pressure chamber 41 or also outside on the envelope 42 of the pressure chamber 41. The detected characteristic pressure values are evaluated by an evaluation unit of the pressure regulation unit 43 not shown in any greater detail. The evaluation unit here is included in the control unit 51 of the pressure regulation unit 43. At a pressure within the pressure chamber 41 of less than 0.3 bar, controlled by the control unit 51, the pressure chamber 41 is filled with compressed air by means of the pressure supply unit 44. At a pressure within the pressure chamber 41 of greater than 0.5 bar, controlled by the control unit 51, compressed air is vented from the pressure chamber 41 by means of the valve unit 45.

The pressure regulation unit 43 also includes an alarm signal unit 47, by means of which an alarm signal is output for the operator of the medical imaging apparatus 10, as soon as the pressure within the pressure chamber 41 lies outside a permitted pressure range. For this purpose the sensed data of the sensor unit 46 is conveyed to the evaluation unit of the pressure unit 40 and is evaluated there. In this process a pressure within the pressure chamber 41 is determined on the basis of the sensed characteristic pressure values. If this current pressure present within the pressure chamber 41 of the pressure unit 40 lies below a lower limit value or above an upper limit value, an alarm signal is generated by the alarm signal unit 47 and this is output via an alarm signal output unit of the alarm signal unit 47 not shown in any greater detail. The lower limit value has a value of 0.1 bar and the upper limit value a value of 1.0 bar.

The alarm signal output unit in this case can comprise both optical alarm output device(s), such as a monitor for example, for output of optical alarm signals, and also acoustic alarm output device(s) for output of acoustic alarm signals. The alarm signal output unit can also be embodied in one piece with the display unit 31 and/or an output unit of the medical imaging apparatus 10.

The alarm signal unit 47 and the pressure supply unit 44 are arranged outside a detection area of the medical imaging apparatus 10. The pressure supply unit 44 in this case is connected by way of supply lines, such as compressed air lines for example, to the pressure chamber 41 of the pressure unit 40. The supply lines of the pressure unit 40 are for example disposed in an area of cables leading to the PET detector unit 22 so that the supply lines of the pressure unit 40 can especially be disposed in a space-saving and compact manner within the medical imaging apparatus 10.

The pressure chamber 41, after being filled with the fluid, occupies a space between the PET detector unit 22 and the gradient coil unit 14, so that a direct coupling of vibrations and/or sound waves between the gradient coil unit 14 and the PET detector unit 22 is suppressed. In addition, as a result of the separate pressure chamber 41 within the pressure unit 40, a uniform, even pressure is exerted on the individual detector elements 24 of the PET detector unit 22.

Figure 3:
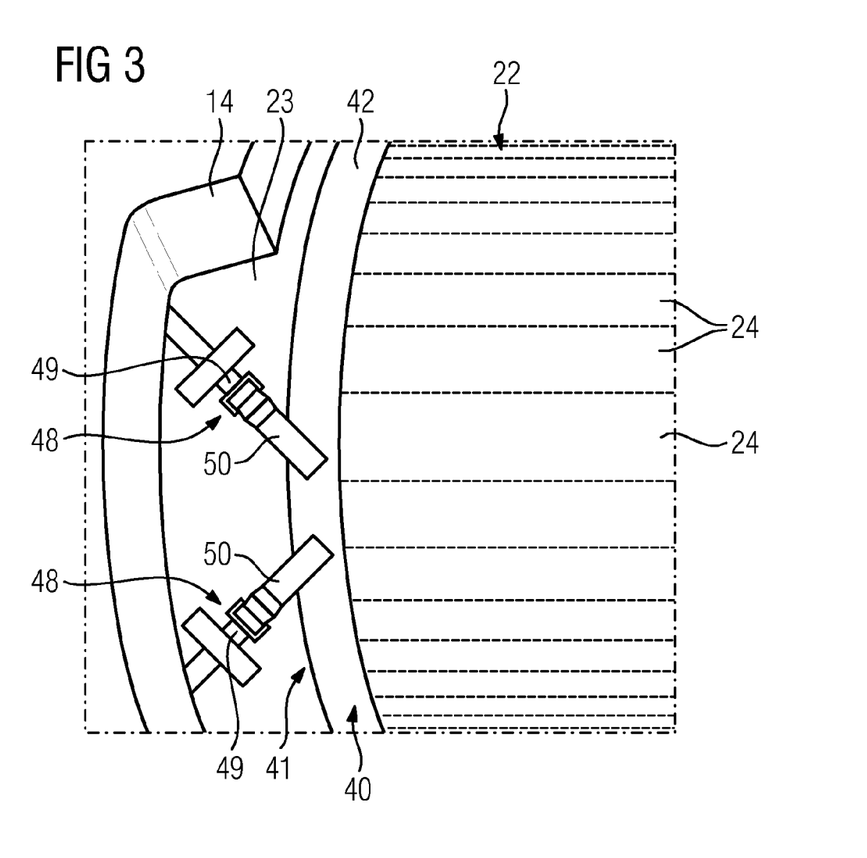
FIG. 3 shows a part area of a carrier unit of the PET apparatus and of the PET detector with the pressure unit and FIG. 4 shows an alternative embodiment of the pressure unit to FIGS. 2 and 3.

The PET apparatus 21 also features an attachment unit 48 for attaching the pressure chamber 41 of the pressure unit 40, especially the pressure chamber 41 of the pressure unit 40, to the carrier unit 23 for support of the PET detector unit 22 (FIG. 3). The attachment unit 48 in the present example embodiment has a number of attachment elements 49, 50. Two of the attachment elements 49, 50 in each case make a connection for attaching the pressure chamber 41. The attachment elements 49, 50 are each formed by fabric strips with a latching element, wherein the two latching elements of the two attachment elements 4950 making a connection are embodied correspondingly. The PET detector unit 22 with the individual PET detectors is shown as a dashed outline in FIG. 3 because it is covered by the pressure chamber 41 of the pressure unit 40.

By way of the latching elements of the attachment elements 49, 50 the pressure chamber 41 is disposed releasably and/or detachably on the carrier unit 23 for support of the PET detector unit 22, so that the pressure chamber 41 can be removed at any time from the carrier unit 23, for example for installation work on the PET detector 22, without this adversely affecting the operability of the pressure chamber 41 and/or of the carrier unit 23 and/or of the PET detector unit 22.

At least one of the respective two attachment elements 49, 50 of the attachment unit 48 making a connection has a bracing element by which the pressure chamber 41, especially the variable and/or deformable envelope 42 of the pressure chamber 41 made of polyurethane foil, can be braced into a position disposed on the carrier unit 23 for support of the PET detector unit 22. The pressure chamber 41 after attachment to the carrier unit 23 to support the PET detector unit 22, can be braced by this by means of the bracing element such that the pressure chamber 41 is especially supported without any folds on the PET detector unit 22. The bracing elements can be embodied in one piece with the latching elements, wherein for example a length of the fabric strip is able to be set by way of the bracing elements.

The individual attachment elements 49, 50 of the attachment unit 48 are glued onto the carrier unit 23 of the PET apparatus 21 and/or onto the pressure chamber 41. As an alternative to this the individual attachment elements 49, 50 can also be disposed in a further manner appearing sensible to the person skilled in the art on the carrier unit 23 of the PET apparatus 21 and/or on the pressure chamber 41. In addition it is also conceivable for an embodiment of the attachment elements 49, 50 to differ from the example embodiment described here.

The pressure chamber 41 is attached to the carrier unit 23 of the PET apparatus 21 by means of the attachment unit 48, wherein in this case the carrier unit 23 together with the PET detector unit 22 supported on the carrier unit 23 is disposed outside of the detection area of the medical imaging apparatus 10 and also outside an area disposed between the high-frequency coil unit 16 and the gradient coil unit 14 for accommodating the PET detector unit 22. The pressure chamber 41 is in an unfilled state for attachment to the carrier unit 23 of the PET apparatus 21. After the pressure chamber 41 has been correctly positioned and disposed on the carrier unit 23 and the PET detector unit 22, the carrier unit 23 of the PET apparatus 21 together with the PET detector unit 22 and the pressure chamber 41 will be introduced in an installation step into the area between the high-frequency coil unit 16 and the gradient coil unit 14. Only when the pressure chamber 41 of the pressure unit 40 is disposed within the annular gap 25 between the PET detector unit 22 and the gradient coil unit 14 will the pressure chamber 41 be filled with compressed air by way of the pressure supply unit 44.

Figure 4:
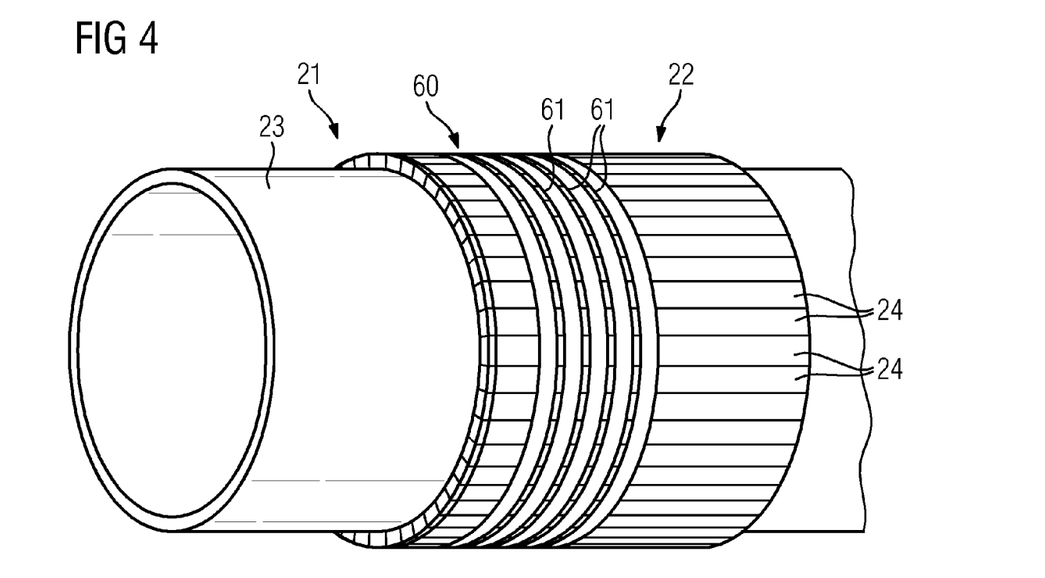

FIG. 4 shows an alternative exemplary embodiment of a pressure unit 60 of the medical imaging apparatus 10. Components, features and functions which are essentially the same are basically labeled with the same reference characters. The description below is essentially restricted to the differences from the example embodiment in FIGS. 2 and 3 wherein, in relation to components, features and functions that remain the same, the reader is referred to the description of the exemplary embodiment in FIGS. 2 and 3.

FIG. 4 shows a PET apparatus 21 together with the pressure unit 60 of a medical imaging apparatus 10. The PET apparatus 21 of the medical imaging apparatus 10, except for the embodiment of the pressure unit 60, is embodied similar to the description in FIGS. 2 and 3. Likewise a further embodiment of the medical imaging apparatus 10 not shown in any greater detail in FIG. 4, corresponds to the description for the example embodiment of FIGS. 2 and 3.

The pressure unit 60 in this example embodiment has a number of elastic tensioning bands 61 which are disposed around a PET detector unit 22 of the PET apparatus 21 in a circumferential direction of a carrier unit 23 for support of the PET detector unit 22. The individual elastic bands 61 are disposed next to one another on the PET detector unit 22. A number of bands 61 are designed such that the bands 61 disposed next to one another 61 if possible cover an entire detector surface of the PET detector unit 22, wherein only five of the tensioning bands 61 are shown in FIG. 4 by way of example. The tensioning bands 61 are also tensioned by means of a tensioning unit not shown in any greater detail so that the individual tensioning bands 61 rests with essentially the same pressure on the individual PET detector elements 24 of the PET detector unit 22.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical imaging apparatus comprising:
   a first imaging modality, formed by a magnetic resonance including a cylindrical gradient coil unit; and
   a further imaging modality, including
      a detector unit, the detector unit of the further imaging modality being supported in a radial direction within an area surrounded by the gradient coil unit and an annular gap being disposed between the detector unit of the further imaging modality and the gradient coil unit,
      a pressure unit disposed in the annular gap between the detector unit of the further imaging modality and the gradient coil unit,
      a carrier unit configured to support the detector unit of the further imaging modality, and
      a latching mechanism configured to attach the pressure unit to the carrier unit of the further imaging modality.

2. The medical imaging apparatus of claim 1, wherein the pressure unit includes a single pressure chamber, which, in an installed position, is configured to completely cover the detector unit of the further imaging modality.

3. The medical imaging apparatus of claim 1, wherein the pressure unit includes a pressure chamber with a pressure of at least 0.1 bar therein.

4. The medical imaging apparatus of claim 1, wherein the pressure unit includes a pressure chamber with a pressure of maximum of 1.0 bar therein.

5. The medical imaging apparatus of claim 1, wherein the pressure unit includes a pressure chamber which comprises an envelope with a variable shape.

6. The medical imaging apparatus of claim 2, wherein the pressure chamber is configured to be filled with a fluid.

7. The medical imaging apparatus of claim 1, wherein the pressure unit includes a pressure regulation unit.

8. The medical imaging apparatus of claim 1, wherein the pressure unit includes at least one sensor element configured to monitor a characteristic pressure value.

9. The medical imaging apparatus of claim 1, wherein the pressure unit includes an alarm signal unit configured to generate an alarm signal and issue the signal upon at least one of the pressure falling below a relatively lower limit value and the pressure exceeding a relatively upper limit value.

10. The medical imaging apparatus of claim 1, wherein the pressure unit is attached to the carrier unit of the further imaging modality by way of the latching mechanism before the carrier unit of the further imaging modality is installed within the annular gap.

11. The medical imaging apparatus of claim 10, wherein the pressure unit is installed in the annular gap in a position mounted on the carrier unit of the further imaging modality.

12. The medical imaging apparatus of claim 1, wherein the latching mechanism includes at least one attachment element configured to brace a pressure chamber of the pressure unit on the detector unit of the further imaging modality.

13. The medical imaging apparatus of claim 1, wherein the latching mechanism includes at least one attachment element configured to releasably attach a pressure chamber of the pressure unit to the carrier unit of the further imaging modality.

14. The medical imaging apparatus of claim 1, wherein the latching mechanism includes at least two attachment elements configured to make a connection to attach the pressure unit to the carrier unit of the further imaging modality, wherein a first of the at least two attachment elements is disposed on the pressure unit and a second of the at least two attachment elements is disposed on the carrier unit of the further imaging modality.

* * * * *